United States Patent [19]
DeVries et al.

[11] Patent Number: 6,031,114
[45] Date of Patent: Feb. 29, 2000

[54] PROCESS FOR PYRROLIDINYL HYDROXAMIC ACID COMPOUNDS

[75] Inventors: Keith M. DeVries, Chester; Brian C. Vanderplas, Old Lyme, both of Conn.

[73] Assignee: Pfizer Inc., New York, N.Y.

[21] Appl. No.: 09/374,869

[22] Filed: Aug. 16, 1999

Related U.S. Application Data

[60] Provisional application No. 60/097,633, Aug. 24, 1998.
[51] Int. Cl.[7] .................................................. C07D 207/12
[52] U.S. Cl. ............................................................. 548/556
[58] Field of Search ............................................. 548/556

[56] References Cited

FOREIGN PATENT DOCUMENTS

| WO 95/32198 | 11/1995 | WIPO | ........................... C07D 403/14 |
| 96/30339 | 3/1996 | WIPO . | |
| WO 98/12177 | 3/1998 | WIPO | ........................... C07D 207/12 |

OTHER PUBLICATIONS

*Tetrahedron Letters*, vol. 37, No. 31, pp. 5619–5622, 1996, O'Brien, et al., "A Simple and Efficient Method for the Preparation of homochiral Amines: Application to the Synthesis of a New $C_2$ Symmetric Triamine".

*J. Org. Chem.*, 1995, 60, 8424–8427, Miao, et al, "Influence of the Aromatic Substituent on the Reactivity of (R)–N–Methyl–1–phenyl–2–(1–piperidinyl)ethanamine Cuprates in Enantioselective Conjugate Addition[1]".

*Tetrahedron: Asymmetry*, vol. 8, No. 15, pp. 2613–2618, 1997, de Sousa, et al, Two useful methods for the preparation of (R)–and (S)–N–methyl–1–phenyl–2–(1–pyrrolidinyl)enthanamine.

Letters Synlett, Feb. 1990, pp. 109–110, Synthesis of Chiral Triamine Ligands from Ephedrine and Pseudoephedrine.

*Primary Examiner*—Johann Richter
*Assistant Examiner*—Dominic Keating
*Attorney, Agent, or Firm*—Peter C. Richardson; Gregg C. Benson; Mervin E. Brokke

[57] ABSTRACT

A method for preparing hydroxamic acid derivatives which are useful as analgesic, antiinflammatory, or neuroprotective agents.

3 Claims, No Drawings

PROCESS FOR PYRROLIDINYL HYDROXAMIC ACID COMPOUNDS

THIS APPLICATION CLAIMS THE PRIORITY BENEFIT OF U.S. PROVISIONAL APPLICATION Ser. No. 60/097,333 filed Aug. 24, 1998.

FIELD OF THE INVENTION

This invention relates a novel process for preparing hydroxamic acid derivatives and their pharmaceutically acceptable salts. These compounds and compositions are useful as analgesic, antiinflammatory, diuretic, anesthetic or neuroprotective agents, or as agents for treatment of stroke or functional bowel diseases such as abdominal pain, for the treatment of a mammalian subject, especially a human subject.

BACKGROUND ART

Opioid analgesics such as morphine are therapeutically useful, but their usage is strictly limited because of their side effects such as drug dependency. Thus, analgesics with high usefulness and reduced tendency to cause drug dependency are desired. Considerable pharmacological and biochemical studies have been carried out to discover the opioid peptides and opioid receptors, and the discovery of the subtype of opioid receptor such as μ, δ, κ at a peripheral nerve in a variety of species, including human, has made a beginning towards creating new analgesics. As it is thought that opioid analgesics such as morphine act as a Preceptor agonist, separating the action based on a κ-receptor agonist from the action based on μ-receptor agonist has been investigated. Recently κ-selective agonists have been reported from the above viewpoint for example, EMD-60400: A. Barber et al., Naunyn-Schmled. Arch. Pharmacol., 345 (Suppl.): Abst 456. Some of them have been studied in clinical trials (Med. Res. Rev., 12, 525 (1992)).

WO 96/30339 describes a compound of the formula:

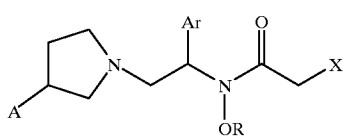

(I)

and the salt thereof, wherein

A is hydrogen, hydroxy or OY, wherein Y is a hydroxy protecting group;

Ar is phenyl optionally substituted with one or more (preferably up to three) substitutents selected from halo, hydroxy, $C_1$–$C_4$ alkyl, $C_1$–$C_4$ alkoxy, $CF_3$, $C1$–$C_4$ alkoxy-$C_1$–$C_4$ alkyloxy, and carboxy-$C_1$–$C_4$ alkyloxy;

X is phenyl, naphthyl, biphenyl, indanyl, benzofuranyl, benzothiophenyl, 1-tetralone-6-yl, $C_1$–$C_4$ alkylenedioxy, pyridyl, furyl and thienyl, these groups optionally being substituted with up to three substituents selected from halo, $C_1$–$C_4$ alkyl, $C_1$–$C_4$alkoxy, hydroxy, $NO_2$, $CF_3$ and $SO_2CH_3$; and R is hydrogen, $C_1$–$C_4$ alkyl or a hydroxy protecting group.

The hydroxamic acid derivatives of formula (I), wherein A is hydrogen or hydroxy and R is hydrogen or $C_1$–$C_4$ alkyl, exhibit significant agonist activity toward opioid κ-receptor. Therefore these κ agonists are particularly useful as an analgesic agent in mammals, especially humans. They are also useful as antiinflammatory, diuretic, anesthetic or neuroprotective agents, or an agent for treatment of stroke or functional bowel diseases such as abdominal pain, for the treatment of a mammalian subject, especially a human subject.

BRIEF DESCRIPTION OF THE INVENTION

This invention provides an advantageous synthetic method for the compounds of formula I above wherein A is hydroxy, Ar is phenyl, or phenyl substituted with up to three substituents selected from chloro, methyl and $CF_3$, more preferably 3,4-dichlorophenyl, and R is hydrogen. The preferred configuration of the carbon atom to which the group Ar is attached is (S).

Preferred individual compounds which may be prepared by the process of the invention are:

2-(3,4-Dichlorophenyl)-N-hydroxy-N-[2-(3-(S)-hydroxypyrrolidin-1-yl)-1-(S)-phenylethyl] acetamide;

2-(4-Bromophenyl)-N-hydroxy-N-[2-(3-(S)-hydroxypyrrolidin-1-yl)-1-(S)-phenylethyl] acetamide;

N-Hydroxy-N-[2-(3-(S)-hydroxypyrrolidin-1-yl)-1-(S)-phenylethyl]-2-(4-trofluoromethylphenyl)acetamide;

2-(4-Chlorophenyl)-N-hydroxy-N-[2-(3-(S)-hydroxypyrrolidin-1-yl)-1-(S)-phenylehtyl]acetamide;

2-(2,3-Dichlorophenyl)-N-hydroxy-N-[2-(3-(S)-hydroxypyrrolidin-1-yl)-1-(S)-phenylethyl]acetamide;

2-(2,4-Dichlorophenyl)-N-hydroxy-N-[2-(3-(S)-hydroxypyrrolidin-1-yl)-1-(S)-phenylethyl]acetamide;

2-(2,5-Dichlorophenyl)-N-hydroxy-N-[2-(3-(S)-hydroxypyrrolidin-1-yl)-1-(S)-phenylethyl]acetamide;

2-(2,6-Dichlorophenyl)-N-hydroxy-N-[2-(3-(S)-hydroxypyrrolidin-1-yl)-1-(S)-phenylethyl]acetamide;

N-Hydroxy-N-[2-(3-(S)-hydroxypyrrolidin-1-yl)-1-(S)-phenylethyl]-2-(2,3, 6-trichlorophenyl)acetamide;

2-(3,4-Dichlorophenyl)-N-[2-(3-(S)-hydroxypyrrolidin-1-yl)-1-(S)-phenylethyl]acetamide; and 2-(3,4-Dimethylphenyl)-N-hydroxy-N-[2(3-(S)-hydroxypyrrolidin-1-yl)-1-(S)-phenylethyl]acetamide.

This invention also provides novel intermediates which are useful for preparing compounds of Formula I; these intermediates include:

A compound of the structure

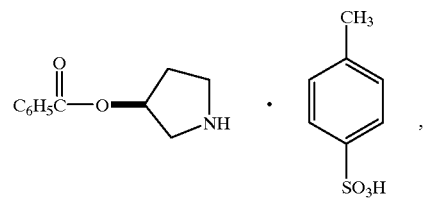

a composition comprising compounds of the structures

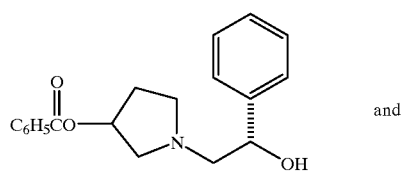

and

-continued
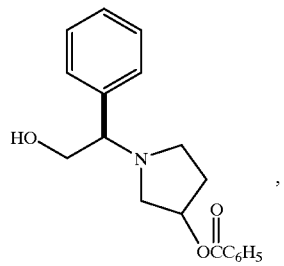
,
a compound of the structure
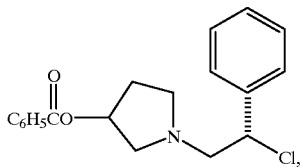
a compound of the structure
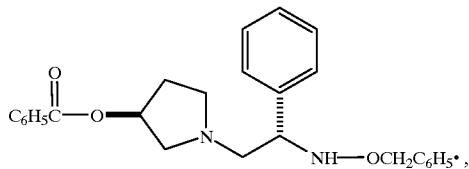
a compound of the structure
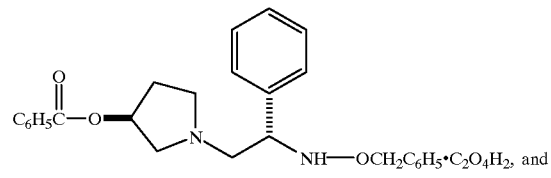
a compound of the structure
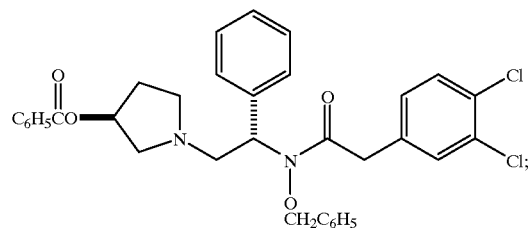
and a compound of the structure
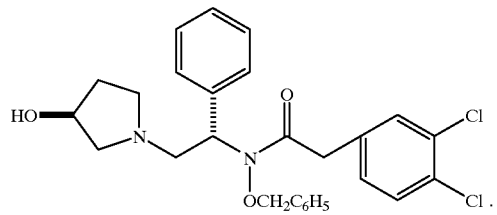
DETAILED DESCRIPTION OF THE INVENTION
Compounds of Formula I may be advantageously prepared by the reaction scheme shown below.
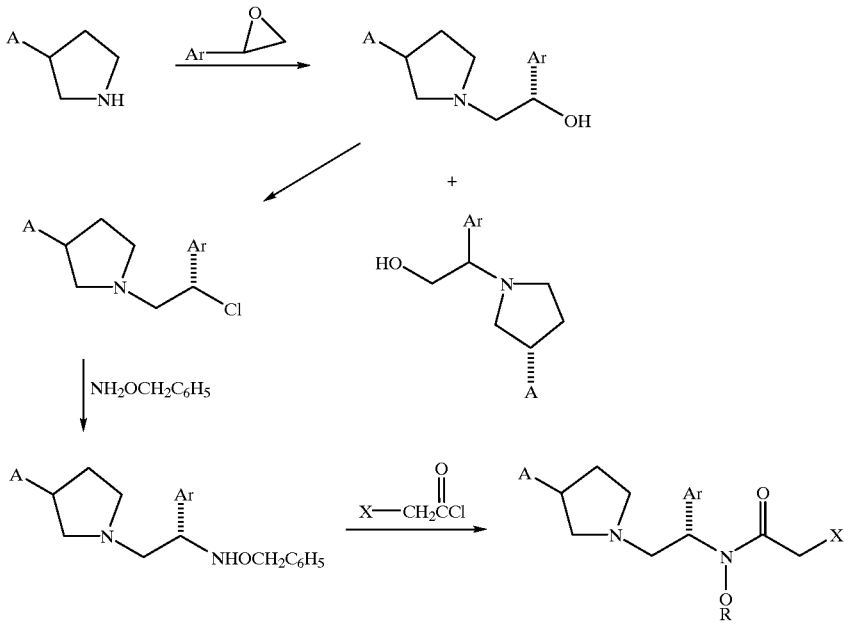

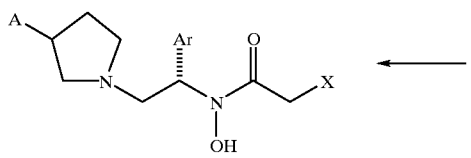
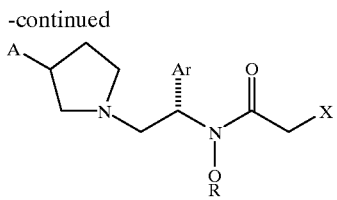

wherein:

A is hydroxy or OY, wherein Y is a hydroxy protecting group;

Ar is phenyl optionally substituted with one or more (preferably up to three) substitutents selected from halo, hydroxy, $C_1$–$C_4$ alkyl, $C_1$–$C_4$ alkoxy, $CF_3$, $C_1$–$C_4$ alkoxy-$C_1$–$C_4$ alkyloxy, and carboxy-$C_1$–$C_4$ alkyloxy;

X is phenyl, naphthyl, biphenyl, indanyl, benzofuranyl, benzothiophenyl, 1-tetralone-6-yl, $C_1$–$C_4$ alkylenedioxy, pyridyl, furyl and thienyl, these groups optionally being substituted with up to three substituents selected from halo, $C_1$–$C_4$ alkyl, $C_1$–$C_4$ alkoxy, hydroxy, $NO_2$, $CF_3$ and $SO_2CH_3$; and R is a benzyl group.

We have found a scheme for the incorporation and removal of protecting groups which render intermediates previously found to be unstable into workable compounds. The benzoyl group has been found to be particularly useful for the Y protecting group. Selective cleavage of the benzyl protected hydroxamic acid requires the choice of an appropriate catalyst.

The compound deprotected in example nine (step 9) contains additional functionality which is not inert to hydrogenation conditions. Specifically, the 3,4-dichlorinated aromatic ring is prone to dehalogenation, and the nitrogen-oxygen bond of the hydroxamic acid moiety has the potential to hydrogenolyze to the secondary amide. These undesired reactions were controlled by the appropriate choice of catalyst and the acid content. A large range of hydrogenation catalysts were screened which minimized the extent of these two side reactions (Johnson Matthey type A111 90A-5 being preferred). In addition, the acid content greatly minimized the extent of dehalogenation. Although additional deoxygenation was observed in the presence of acid, this side product was purged in the subsequent steps. The formation of the specific salts of compounds shown in the following scheme render key intermediates crystalline, making purification feasible.

A detailed scheme for the preparation of 2-(3,4-Dichlorophenyl)-N-hydroxy-N-[1-(S)-phenyl-2(1-pyrrolidinyl)ethyl]acetamide p-methyl phenyl sulfonate is shown below and described in detail in Examples 1–10.

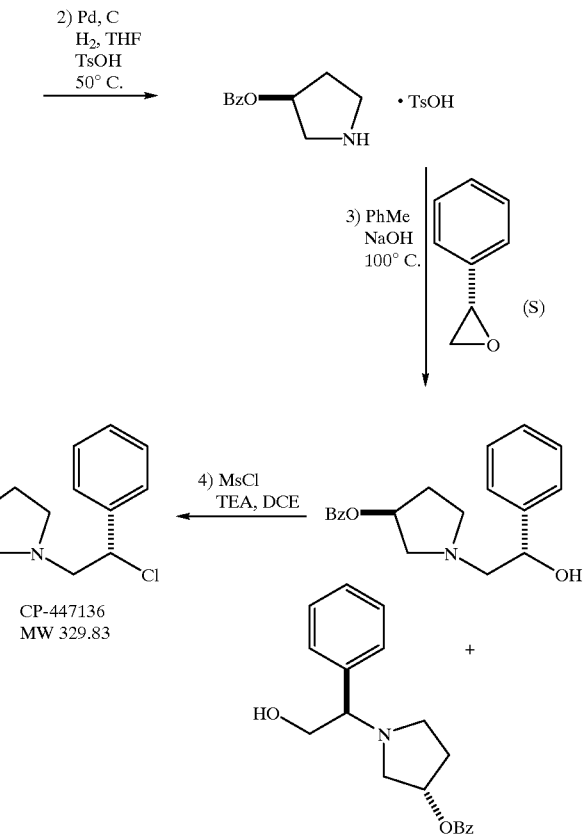

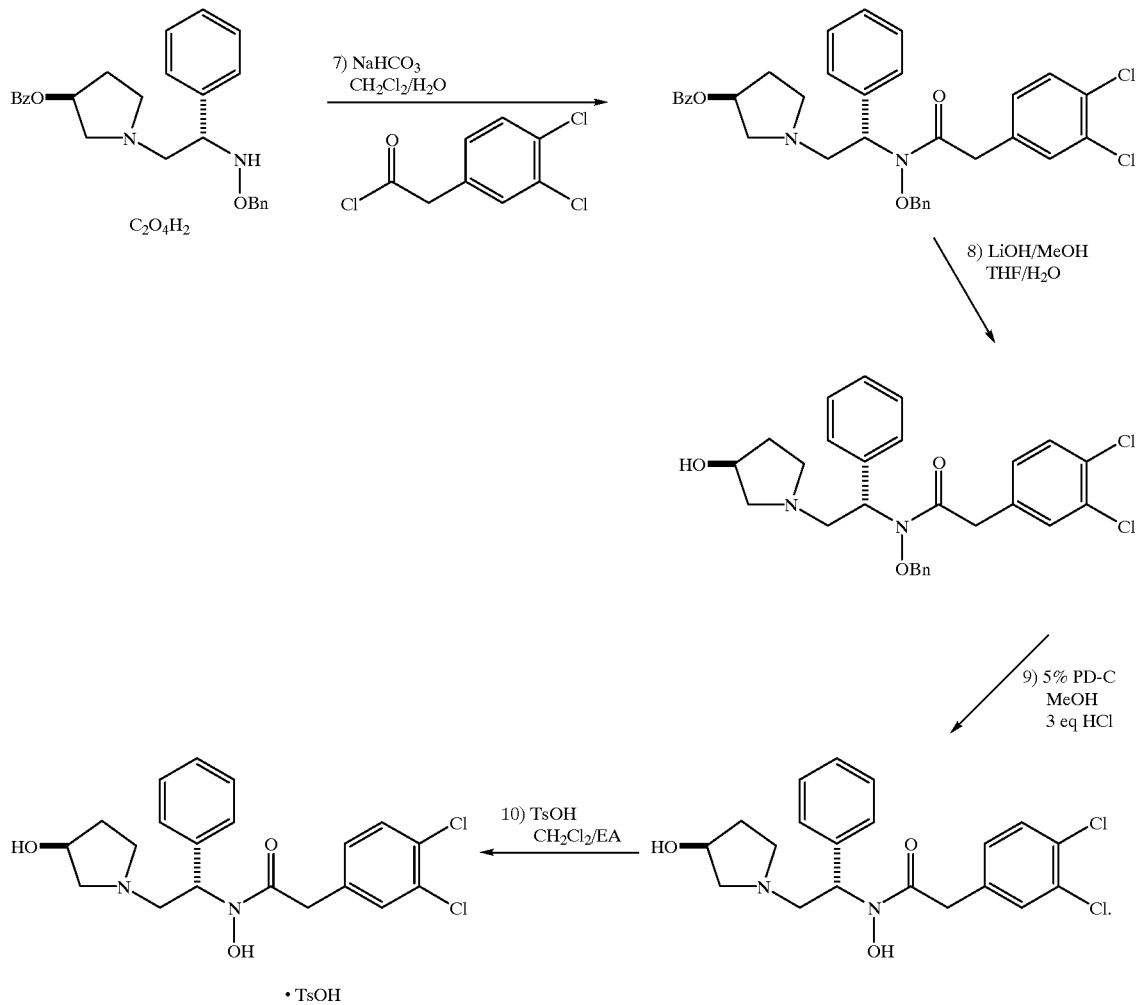

EXAMPLES

The present invention is illustrated by the Examples below. It should be understood that the invention is not limited to the specific details of these examples.

Example 1

Benzoic acid 1-benzyl-2pyrrolidin-3-yl ester

To a solution of 100.0 gm of S-N-Benzyl-3-hydroxypyrrolidine (0.56 mol. 1.0 equiv.) in 500 mL of methylene chloride was added 65.0 mL of benzoyl chloride (0.56 mol, 1.0 equiv) at 0° C. over 15 minutes. The reaction was allowed to stir for an additional hour. HPLC analysis showed that only trace starting material remained. To the resultant yellow slurry at 0° C. was added a solution of 59.4 gm of sodium carbonate (0.56 mol, 1.0 equiv.) dissolved in 500 mL of water. The layers were separated, and the aqueous layer was extracted with another 500 mL of methylene chloride. The volatiles were removed at atmospheric pressure to provide 155.1 gm (98%) of the title compound as an oil, which was used in the next step without additional purification.

Example 2

Benzoic acid pyrrolidin-3yl ester p-methylrhenyl sulfonate

To a solution of 25.0 gm of the compound of Example 1 (89 mmol, 1.0 equiv.) in 250 mL of THF was added 7.5 gm of 10% palladium on carbon (50% water wet) and 16.9 gm (89 mmol, 1.0 equiv.) of tosic acid monohydrate. The mixture was then hydrogenated on a parr shaker at 50 psig and 50° C overnight. In the AM the hydrogen was purged and the mixture filtered through celite to remove the catalyst. HPLC analysis showed that only trace starting material remained. The filter cake was washed with THF and the volatiles were removed under vacuum to provide a slurry. Further displacement of THF with isopropyl ether was followed by filtration and drying under vacuum to provide 30.2 gm (89%) of the title compound as a white solid.

Example 3

Benzoic acid 1- (2-hydroxy-2-rhenyl-ethyl) -pyrrolidin-3-yl ester

To a biphasic mixture of 25.0 gm of the compound of Example 2 (69 mmol, 1.0 equiv.) in 125 mL of toluene was added 2.75 gm of sodium hydroxide (69 mmol, 1.0 equiv.) dissolved in 20 mL of water followed by 8.27 gm (69 mmol, 1.0 equiv.) of (S)-styrene oxide. The reaction mixture was heated to reflux overnight, at which time HPLC analysis showed that only trace starting material remained. Upon cooling to room temperature the layers were separated. The organic layer was washed with an additional 1.4 gm (35 mmol, 0.5 equiv.) of sodium hydroxide dissolved in 20 mL of water followed by another wash with 20 mL of water. The toluene solvent was removed under vacuum to provide 19.77 gm (92%) of a thick oil which solidified on standing. The crude product contained an ~1.2:1.0 mixture of regioisomers and was used without further purification in the next step.

Example 4

Benzioc acid 1- (2-chloro-2-phenyl-ethyl) -pyrrolidin-3-yl ester

To a solution of a mixture of 50.0 gm (161 mmol) of the compound of Example 3 in 500 mL of dichloroethane was added 24.7 mL (177 mmol, 1.1 equiv.) of triethyl amine. At 0 ° C 13.7 ml (177 mmol, 1.1 equiv.) of methanesulphonyl chloride was added dropwise over 20 minutes to keep the temperature <5° C. The mixture was allowed to warm to room temp and after 2.5 hours TLC analysis (silica gel, 254 nm, 60:40 hexanes/ethyl acetate) showed that the starting material was consumed. The solution of the title compound was used directly in the next reaction. For analytical evaluation purposes, a sample of the reaction mixture was washed with aqueous sodium bicarbonate and the volatiles were removed under vacuum to provide the title compound as an oil.

Example 5

Benzoic acid 1- (2-benzyloxyamino-2-phenyl-ethyl)-pyrrolidin-3-yl ester

The solution of the compound of Example 4 was treated with an additional 25.4 mL of triethyl amine (354 mmol, 2.2 equiv.) and 30.8 gm (193 mmol, 1.2 equiv.) of O-benzylhydroxylamine.HCl. The reaction mixture was brought to 50 ° C. and then 100 mL of isopropanol was added to dissolve the O-benzylhydroxylamine HCl. The reaction mixture was allowed to stir overnight at reflux under a nitrogen atmosphere. In the AM, TLC analysis (silica gel, 254 nm, 60:40 hexanes/ethyl acetate) showed that the starting was consumed. The reaction mixture was cooled to room temp and then quenched by the addition of 400 mL of 1 N NaOH (pH of reaction mixture 11). After separation of the layers the organic phase was washed with 250 mL of water. The organic layer was separated and volatiles were removed under vacuum to provide crude CP-447139 as an oil.

Example 6

Benzoic acid 1- (2-benzyloxyamino-2-phenyl-ethyl)-pyrrolidin-3-yl ester oxalate salt The crude oil of Example 5 was dissolved in 500 mL of isopropanol and treated with 20.3 gm (161 mol, 1.0 equiv.) of oxalic acid. 2H$_2$O. The resultant slurry was stirred overnight and then cooled to 0 ° C. and filtered. The wet cake was then reslurried from 300 mL of hot isopropanol. The slurry was allowed to cool to room temp overnight. In the AM the solid was filtered and the product cake washed first with isopropanol and then with isopropylether. The solid was dried under vacuum to provide 48.1 gm (59%) of the title compound as a pale white solid.

Example 7

Benzoic acid N-Benzyloxy-2- (3,4-dichloro-phenyl) -N-[2-(3-hydroxy-pyrrolidin-1-yl) -1-phenyl-ethyl]- acetamide ester To a solution of 899 gm (4.37 mmol) of 3,4-dichlorophenyl acetic acid in 10.5 L of methylene chloride was added 586 gm (4.62 mol, 1.05 equiv.) of oxalyl chloride at room temperature. This was followed by the careful addition of 31 gm (0.42 mol, 0.10 equiv.) of dimethylformamide (beware of gas evolution). After gas evolution subsided, an aliquot was quenched into methanol to insure complete reaction by conversion to the corresponding methyl ester. HPLC analysis showed only trace starting material. The solution of (3,4-Dichloro-phenyl)-acetyl chloride was carried into the next reaction.

To a slurry of 2118 gm (4.18 mol) of the product of Example 6 in 10.5 L of methylene chloride was added a slurry of 1,780 gm (21.1 mol, 5 equiv.) of sodium bicarbonate in 21 L of water (beware of gas evolution). The biphasic mixture was cooled to 0 ° C. and the methylene chloride solution of (3,4-Dichloro-phenyl)-acetyl chloride (4.37 mol, 1.05 equiv.) was added at a rate to keep the temperature less than 10 ° C. The pH was monitored and remained between 8 and 9. After the addition was complete, HPLC analysis showed that the starting material was consumed. An additional 10.5 L of water was added and the reaction was allowed to stir overnight at room temperature. In the AM the agitation was stopped and the layers allowed to separate. The organic layer was collected and concentrated under vacuum to an oil, which was used without further purification in the next step (crude purity 93.9%).

Example 8

N-Benzyloxy-2- (3,4-dichloro-phenyl) -N-[2-(3-hydroxy-pyrrolidin-1-yl) -1-phenyl-ethyl]-acetamide To a solution of the crude product from Example 7 (4.18 mol theory) in 26 L of a 1:1 (v/v) mixture of THF and methanol was added a solution of 356 gm (8.28 mol, 2.0 equiv.) of lithium hydroxide. H$_2$O dissolved in 6.5 L of water. The reaction mixture was stirred overnight at room temperature. In the AM the pH was >13, and HPLC analysis showed that the starting material was consumed. The volatiles were then removed under vacuum, keeping the pot temperature <40 ° C. To the crude product was added 13 L of methylene chloride and 13 L of water. The layers were separated, and the organic phase washed with an additional 13 L of water. The solvent was removed under vacuum to provide the crude product (1,990 gm, 95% of theory over two steps) which was carried directly into the next reaction (crude purity 84.1%).

Example 9

2-(3,4-Dichloro-phenyl)-N-hydroxy-N-[2- (3-hydroxy-nyrrolidin-1-yl) -1-S-phenyl-ethyl]- acetamide A solution of the product of Example 8 (3.98 mol theory) in 40 L of methanol was treated with 995 mL (12 mol, 3 equiv) of conc. HCL and 400 gm of 5% Pd.C (50% water wet, Johnson Matthey type Al 11 90A-5). After evacuating and flushing with nitrogen three times, the hydrogen was adjusted to to give a slight positive pressure. Additional hydrogen was added to maintain a slight positive pressure. The extent of reaction was monitored by TLC (silica gel, 90:10 methylene chloride:methanol doped with ammonium hydroxide, Rf of starting material 0.65, Rf of product 0.30), and the starting material was consumed in ~5 hours. The system was evacuated and flushed with nitrogen three times. The catalyst was removed by filtration through celite followed by a 30 L methanol wash of the catalyst cake. The HCl/MeOH was then neutralized with the careful addition of the product containing solution to 1350 gm (16 mol, 4 equiv.) of sodium bicarbonate dissolved in 10 L of water. The methanol was then removed under vacuum followed by the addition of 4 L of methylene chloride and 2 L of water. After separation of the layers, the organic phase was washed with an additional 10 L of water, separated again, and carried into the salt forming step without additional purification.

Example 10

2-(3,4-Dichlorophenyl)-N-hydroxy-N-[1-(S)-phenyl-2(1-pyrrolidinyl)ethyl]acetamide p-methyl phenyl sulfonate The methylene chloride solution of 2-(3,4-Dichlorophenyl)-N-hydroxy-N-[1-(S)-phenyl-2(1-pyrrolidinyl)ethyl]acetamide (3.98 mol theory) from the previous Example was treated with 757 gm (3.98 mol, 1.0 equiv) of para-toluene sulphonic acid. $H_2O$ and stirred to dissolution. This was followed by filtration through a 0.2 micron filter to remove particulates. The methylene chloride was then displaced with ethyl acetate to a final volume of 6 L. Upon cooling to room temperature, the product precipatited and was left to stir overnight. In the AM the slurry was cooled to 0 ° C. for 90 minutes and filtered. The cake was washed with 2×500 mL of cold ethyl acetate. Upon drying the weight was 1,529 gm, 66% of theory over two steps. The purity by HPLC at this point was 96.5%.

1,514 gm of the solid from above was treated with 7.5 L of water and the slurry was stirred overnight at room temp. The solids were filtered and the cake was washed with 2 L of isopropyl ether. Upon drying, the weight was 1,440 gm (95.1 %, HPLC purity of 97.3%).

1,429 gm of the solid from above was treated with 5 L of 6: 1 ethylacetate:methanol. The slurry was heated until dissolution occurred, and then the solution was cooled to 50 ° C. 3 L of isopropyl ether was added, and then the reaction mixture was cooled and at 30 ° C. a the precipitated. After stirring at 15 ° C. for 2 hours, the product was filtered.

The cake was washed with 2 L of isopropyl ether and then oven dried to provide 1,219 gm of a white solid (85.3%, HPLC purity 99.6%).

We claim:

1. A compound of the structure

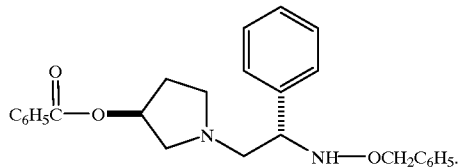

2. A compound of the structure

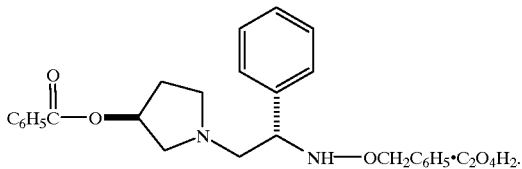

3. A compound of the structure

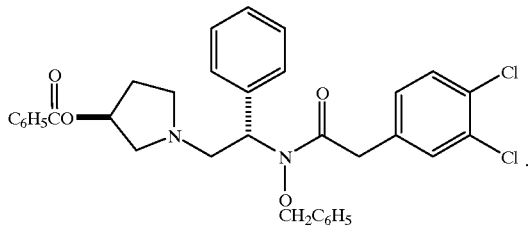

* * * * *